United States Patent
Pantazis et al.

(10) Patent No.: US 10,772,700 B2
(45) Date of Patent: Sep. 15, 2020

(54) CONTACTLESS LOADING UNIT DETECTION

(71) Applicant: Covidien LP, Mansfield, MA (US)

(72) Inventors: John Pantazis, Stratford, CT (US); Anthony Calderoni, Bristol, CT (US)

(73) Assignee: COVIDIEN LP, Mansfield, MA (US)

(*) Notice: Subject to any disclaimer, the term of this patent is extended or adjusted under 35 U.S.C. 154(b) by 164 days.

(21) Appl. No.: 16/043,230

(22) Filed: Jul. 24, 2018

(65) Prior Publication Data

US 2019/0060025 A1 Feb. 28, 2019

Related U.S. Application Data

(60) Provisional application No. 62/549,294, filed on Aug. 23, 2017.

(51) Int. Cl.
*A61B 90/00* (2016.01)
*A61B 90/98* (2016.01)
(Continued)

(52) U.S. Cl.
CPC ........ *A61B 90/06* (2016.02); *A61B 17/07207* (2013.01); *A61B 90/08* (2016.02); *A61B 90/98* (2016.02); *A61B 2017/0046* (2013.01); *A61B 2017/00473* (2013.01); *A61B 2017/00477* (2013.01); *A61B 2017/00876* (2013.01); *A61B 2017/07257* (2013.01); *A61B 2090/0808* (2016.02); *A61B 2090/0811* (2016.02)

(58) Field of Classification Search
CPC ....... A61B 90/08; A61B 90/98; A61B 17/072; A61B 17/068

USPC ...................................................... 227/176.1
See application file for complete search history.

(56) References Cited

U.S. PATENT DOCUMENTS

| 2,777,340 A | 1/1957 | Hettwer et al. |
| 2,957,353 A | 10/1960 | Babacz |

(Continued)

FOREIGN PATENT DOCUMENTS

| AU | 2008229795 A1 | 4/2009 |
| CA | 2451558 A1 | 1/2003 |

(Continued)

OTHER PUBLICATIONS

European Search Report dated Apr. 9, 2019, issued in EP Appln. No. 18190152.

*Primary Examiner* — Nathaniel C Chukwurah
(74) *Attorney, Agent, or Firm* — Carter, DeLuca & Farrell LLP (57) ABSTRACT

A loading unit detection system includes an elongate member, a loading unit, a magnet, and a GMR IC. The elongate member defines a receiver. The loading unit includes a connector that is configured to be received within the receiver to releasably couple the loading unit to the elongate member. The magnet is supported on the connector and is configured to translate relative to the elongate member as the connector is received within the receiver. The GMR IC is embedded within the elongate member and is configured to output a differential voltage in response to a magnetic field produced by the magnet of the loading unit. The differential voltage is indicative of the position of the loading unit within the receiver of the elongate member.

16 Claims, 3 Drawing Sheets

(51) Int. Cl.
*A61B 17/072* (2006.01)
*A61B 17/00* (2006.01)

(56) References Cited

U.S. PATENT DOCUMENTS

| | | |
|---|---|---|
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,467,911 A * | 11/1995 | Tsuruta .............. A61B 17/0682 227/175.1 |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A * | 6/1996 | Boiarski ................ A61B 90/98 227/175.1 |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,632,432 A | 5/1997 | Schulze et al. |
| 5,647,526 A | 7/1997 | Green et al. |
| 5,653,374 A | 8/1997 | Young et al. |
| 5,658,300 A | 8/1997 | Bito et al. |
| 5,667,517 A | 9/1997 | Hooven |
| 5,693,042 A | 12/1997 | Boiarski et al. |
| 5,704,534 A | 1/1998 | Huiterna et al. |
| 5,713,505 A | 2/1998 | Huiterna |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,797,536 A | 8/1998 | Smith et al. |
| 5,820,009 A | 10/1998 | Melling et al. |
| 5,863,159 A | 1/1999 | Lasko |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,326,884 B1 | 12/2001 | Wohlrabe |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,899,538 B2 | 5/2005 | Matoba |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |

(56) References Cited

U.S. PATENT DOCUMENTS

| | | |
|---|---|---|
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,114,118 B2 | 2/2012 | Knodel et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,342,379 B2 | 1/2013 | Whitman et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,424,739 B2 | 4/2013 | Racenet et al. |
| 8,443,476 B2 | 5/2013 | Hilscher et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,551,076 B2 | 10/2013 | Duval et al. |
| 8,561,871 B2 | 10/2013 | Rajappa et al. |
| 8,623,000 B2 | 1/2014 | Humayun et al. |
| 8,632,463 B2 | 1/2014 | Drinan et al. |
| 8,647,258 B2 | 2/2014 | Aranyi et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,758,391 B2 | 6/2014 | Swayze et al. |
| 8,806,973 B2 | 8/2014 | Ross et al. |
| 8,851,355 B2 | 10/2014 | Aranyi et al. |
| 8,858,571 B2 | 10/2014 | Shelton, IV et al. |
| 8,875,972 B2 | 11/2014 | Vveisenburgh, II et al. |
| 8,893,946 B2 | 11/2014 | Boudreaux et al. |
| 8,899,462 B2 | 12/2014 | Kostrzewski et al. |
| 8,939,344 B2 | 1/2015 | Olson et al. |
| 8,960,519 B2 | 2/2015 | Whitman et al. |
| 8,961,396 B2 | 2/2015 | Azarbarzin et al. |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,055,943 B2 | 6/2015 | Zemlok et al. |
| 9,064,653 B2 | 6/2015 | Prest et al. |
| 9,113,875 B2 | 8/2015 | Viola et al. |
| 9,216,013 B2 | 12/2015 | Scirica et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0111012 A1 | 6/2004 | Whitman |
| 2004/0133189 A1 | 7/2004 | Sakurai |
| 2004/0193146 A1 | 9/2004 | Lee et al. |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |
| 2006/0278680 A1 | 12/2006 | Viola et al. |
| 2007/0023476 A1 | 2/2007 | Whitman et al. |
| 2007/0023477 A1 | 2/2007 | Whitman et al. |
| 2007/0029363 A1 | 2/2007 | Popov |
| 2007/0055219 A1 | 3/2007 | Whitman et al. |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0147089 A1 | 6/2008 | Loh et al. |
| 2008/0167671 A1 | 7/2008 | Giordano et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0090763 A1 | 4/2009 | Zemlok et al. |
| 2009/0099876 A1 | 4/2009 | Whitman |

(56) References Cited

U.S. PATENT DOCUMENTS

| | | |
|---|---|---|
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209990 A1 | 8/2009 | Yates et al. |
| 2009/0254094 A1 | 10/2009 | Knapp et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2010/0268250 A1 | 10/2010 | Stuart et al. |
| 2011/0017801 A1 | 1/2011 | Zemlok et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174099 A1 | 7/2011 | Ross et al. |
| 2011/0184245 A1 | 7/2011 | Xia et al. |
| 2011/0204119 A1 | 8/2011 | McCuen |
| 2011/0208170 A1 | 8/2011 | Hafner et al. |
| 2011/0218522 A1 | 9/2011 | Whitman |
| 2011/0253765 A1 | 10/2011 | Nicholas et al. |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0018361 A1 | 1/2013 | Bryant |
| 2013/0075443 A1 | 3/2013 | Giordano et al. |
| 2013/0093149 A1 | 4/2013 | Saur et al. |
| 2013/0098966 A1 | 4/2013 | Kostrzewski et al. |
| 2013/0098968 A1 | 4/2013 | Aranyi et al. |
| 2013/0098969 A1 | 4/2013 | Scirica et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0240596 A1 | 9/2013 | Whitman |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0005681 A1 | 1/2014 | Gee et al. |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0144970 A1 | 5/2014 | Aranyi et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236173 A1 | 8/2014 | Scirica et al. |
| 2014/0236174 A1 | 8/2014 | Williams et al. |
| 2014/0276932 A1 | 9/2014 | Williams et al. |
| 2014/0373652 A1 | 12/2014 | Zergiebel et al. |
| 2015/0157321 A1 | 6/2015 | Zergiebel et al. |
| 2015/0164502 A1 | 6/2015 | Richard et al. |
| 2015/0209035 A1* | 7/2015 | Zemlok ............ A61B 17/07207 73/1.01 |
| 2015/0272577 A1 | 10/2015 | Zemlok et al. |
| 2015/0297199 A1 | 10/2015 | Nicholas et al. |
| 2015/0303996 A1* | 10/2015 | Calderoni ............... A61B 90/98 307/104 |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |

FOREIGN PATENT DOCUMENTS

| | | |
|---|---|---|
| CN | 102247182 A | 11/2011 |
| DE | 102008053842 A1 | 5/2010 |
| EP | 0634144 A1 | 1/1995 |
| EP | 0648476 A1 | 4/1995 |
| EP | 0686374 A2 | 12/1995 |
| EP | 0705571 A1 | 4/1996 |
| EP | 1690502 A1 | 8/2006 |
| EP | 1723913 A1 | 11/2006 |
| EP | 1736112 A1 | 12/2006 |
| EP | 1769754 A1 | 4/2007 |
| EP | 1772105 A1 | 4/2007 |
| EP | 1813199 A1 | 8/2007 |
| EP | 1813203 A2 | 8/2007 |
| EP | 1813211 A2 | 8/2007 |
| EP | 1943954 A2 | 7/2008 |
| EP | 1943956 A2 | 7/2008 |
| EP | 1943958 A1 | 7/2008 |
| EP | 1943976 A2 | 7/2008 |
| EP | 2005898 A2 | 12/2008 |
| EP | 2027819 A1 | 2/2009 |
| EP | 2044890 A1 | 4/2009 |
| EP | 2055243 A2 | 5/2009 |
| EP | 2098170 A2 | 9/2009 |
| EP | 2100561 A2 | 9/2009 |
| EP | 2100562 A2 | 9/2009 |
| EP | 2165664 A2 | 3/2010 |
| EP | 2236098 A2 | 10/2010 |
| EP | 2263568 A2 | 12/2010 |
| EP | 2272443 A1 | 1/2011 |
| EP | 2316345 A1 | 5/2011 |
| EP | 2324776 A2 | 5/2011 |
| EP | 2329773 A1 | 6/2011 |
| EP | 2333509 A1 | 6/2011 |
| EP | 2462878 A1 | 6/2012 |
| EP | 2462880 A2 | 6/2012 |
| EP | 2491872 A1 | 8/2012 |
| EP | 2586382 A2 | 5/2013 |
| EP | 2606834 A2 | 6/2013 |
| EP | 2668910 A2 | 12/2013 |
| EP | 2676615 A2 | 12/2013 |
| EP | 2684530 A1 | 1/2014 |
| EP | 2923653 A2 | 9/2015 |
| EP | 2992839 A2 | 3/2016 |
| EP | 3064146 A1 | 9/2016 |
| ES | 2333509 A1 | 2/2010 |
| JP | 08038488 | 2/1996 |
| JP | 2005125075 A | 5/2005 |
| JP | 2016011864 A | 1/2016 |
| KR | 20120022521 A | 3/2012 |
| WO | 9915086 A1 | 4/1999 |
| WO | 0072760 A1 | 12/2000 |
| WO | 0072765 A1 | 12/2000 |
| WO | 03000138 A2 | 1/2003 |

(56) References Cited

FOREIGN PATENT DOCUMENTS

| | | |
|---|---|---|
| WO | 03013372 A2 | 2/2003 |
| WO | 03026511 A1 | 4/2003 |
| WO | 03030743 A2 | 4/2003 |
| WO | 03065916 A1 | 8/2003 |
| WO | 03077769 A1 | 9/2003 |
| WO | 03090630 A2 | 11/2003 |
| WO | 2004107989 A1 | 12/2004 |
| WO | 2006042210 A2 | 4/2006 |
| WO | 2007016290 A2 | 2/2007 |
| WO | 2007/026354 A1 | 3/2007 |
| WO | 2007137304 A2 | 11/2007 |
| WO | 2008131362 A2 | 10/2008 |
| WO | 2008133956 A2 | 11/2008 |
| WO | 2009039506 A1 | 3/2009 |
| WO | 2007014355 A3 | 4/2009 |
| WO | 2009132359 A2 | 10/2009 |
| WO | 2009143092 A1 | 11/2009 |
| WO | 2009149234 A1 | 12/2009 |
| WO | 2011108840 A2 | 9/2011 |
| WO | 2012/040984 A1 | 4/2012 |
| WO | 2014134027 A2 | 9/2014 |

\* cited by examiner

CONTACTLESS LOADING UNIT DETECTION

CROSS-REFERENCE TO RELATED APPLICATIONS

This application claims the benefit of and priority to U.S. Provisional Patent application Ser. No. 62/549,294 filed Aug. 23, 2017, the entire disclosure of which is incorporated by reference herein.

BACKGROUND

1. Technical Field

The present disclosure relates to surgical instruments and, more specifically, to surgical instruments having contactless detection systems for determining connection between components of the surgical instrument.

2. Discussion of Related Art

Surgical instruments having a handle and a loading unit releasably coupled to the handle are known. Generally, the loading unit receives mechanical input from the handle to actuate a tool of the loading unit.

Some surgical instruments include a detection system to identify and notify a clinician when the loading unit is properly coupled to the handle. Generally, the detection system includes contacts and a mechanical switch. In such instruments, the contacts may be exposed to bodily fluids, e.g., blood or saline. This fluid exposure may result in malfunctioning of the detection system.

In addition, surgical instruments that include detection systems having exposed contacts may be damaged during resterilazation of the surgical instruments. More specifically, during an autoclave process, exposed electrical contacts may be susceptible to damage from the steam and the high-pressure fluids used in the autoclave process. For example, during the autoclave process the exposed electrical contacts may corrode, form dendtric growths, or electro-plate.

Accordingly, a continuing need exists for detection systems that are not susceptible fluid ingress and/or damage from a resterilization process.

SUMMARY

In an aspect of the present disclosure, a loading unit detection system includes an elongate member, a loading unit, a magnet, and a giant magneto-resistance integrated circuit ("GMR IC"). The elongate member defines a receiver. The loading unit includes a connector that is configured to be received within the receiver to releasably couple the loading unit to the elongate member. The magnet is supported on the connector and is configured to translate relative to the elongate member as the connector is received within the receiver. The GMR IC is embedded within the elongate member and is configured to output a differential voltage in response to a magnetic field produced by the magnet of the loading unit. The differential voltage is indicative of the position of the loading unit within the receiver of the elongate member. The magnet may be embedded within the connector of the loading unit.

In aspects, the loading unit detection system includes a secondary magnet that is embedded within the loading unit such that the differential voltage of the GMR IC induced by a combined magnetic field of the magnet and the secondary magnet is indicative of the position of the loading unit within the receiver of the elongate member and the type of the loading unit.

In some aspects, the loading unit detection system includes an operational amplifier and a latch. The operational amplifier may receive the differential voltage from the GMR IC and transmit an amplified output to the latch. The latch may have a first state when the amplified output is below a threshold and a second state when the amplified output is above the threshold. The amplified output may be below the threshold when the connector is in an uncoupled state with the receiver and above the threshold when the receiver is in a coupled state with the receiver. The operation amplifier and the latch may be integrated with the GMR IC.

In certain aspects, the loading unit detection system includes an instrument amplifier and a filter. The instrument amplifier receives the differential voltage from the GMR IC and outputs an amplified signal to the filter. The filter may be configured to output a filtered signal indicative of the position of the connector relative to the receiver and a type of the loading unit.

In another aspect of the present disclosure, a surgical instrument includes a handle, an adapter, a loading unit, and a loading unit detection system. The adapter is releasably coupled to the handle. The loading unit is releasably coupled to the adapter. The loading unit detection system is configured to detect coupling of the loading unit to the adapter. The loading unit detection system includes a magnet and a GMR IC. The magnet is supported on the loading unit and translates relative to the elongate member as the loading unit is coupled to the adapter. The GMR IC is embedded within the adapter and is configured to output a differential voltage in response to a magnetic field produced by the magnet of the loading unit. The differential voltage produced by the GMR IC is indicative of the position of the loading unit within the elongate member.

In aspects, the adapter defines a receiver and the loading unit includes a connector. The connector may be received within the receiver to releasably couple the loading unit to the adapter. The magnet may be embedded within the connector of the loading unit. The GMR IC may be embedded within the receiver of the adapter.

In some aspects, the surgical instrument includes a microprocessor that is disposed within the handle. The microprocessor may receive a signal from the GMR IC that is indicative of the position of the loading unit relative to the adapter. The signal received by the microprocessor may be indicative of the type of loading unit.

Further, to the extent consistent, any of the aspects described herein may be used in conjunction with any or all of the other aspects described herein.

In a further aspect of the present disclosure, a surgical loading unit includes a pair of jaws, one of the jaws including a staple cartridge, and the other of the jaws having an anvil for forming staples. The loading unit has a loading unit detection system that includes a device for outputting an electromagnetic field. The loading unit is configured for use in a surgical system that includes a sensor for sensing the electromagnetic field, and communicating information about the loading unit to a microprocessor that is part of the surgical system. The loading unit can include an elongate member, and the detection system can be mounted on the elongate member, or the detection system can be mounted on the jaws. The detection system can be a giant magneto-resistance integrated circuit ("GMR IC"). The surgical system can include an elongate member defining a receiver and the loading unit can include a connector that is configured to be received within the receiver to releasably couple the loading unit to the elongate member. The magnet is supported on the connector. The magnet can be configured to translate relative to the elongate member as the connector is received within the receiver. The GMR IC is configured to output a differential voltage in response to a magnetic field produced by the magnet of the loading unit. The differential voltage can be indicative of the position of the loading unit within the receiver of the elongate member, indicative of characteristics of the loading unit, and can convey other information. The magnet may be embedded within the connector of the loading unit.

BRIEF DESCRIPTION OF THE DRAWINGS

Various aspects of the present loading unit detection systems for surgical instruments are described hereinbelow with reference to the drawings, which are incorporated in and constitute a part of this specification, wherein.

DETAILED DESCRIPTION

Embodiments of the present loading unit detection systems for surgical instrumentsare now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to that portion of the device or component thereof that is closest to the clinician and the term "distal" refers to that portion of the device or component thereof that is farthest from the clinician.

Figure 1:
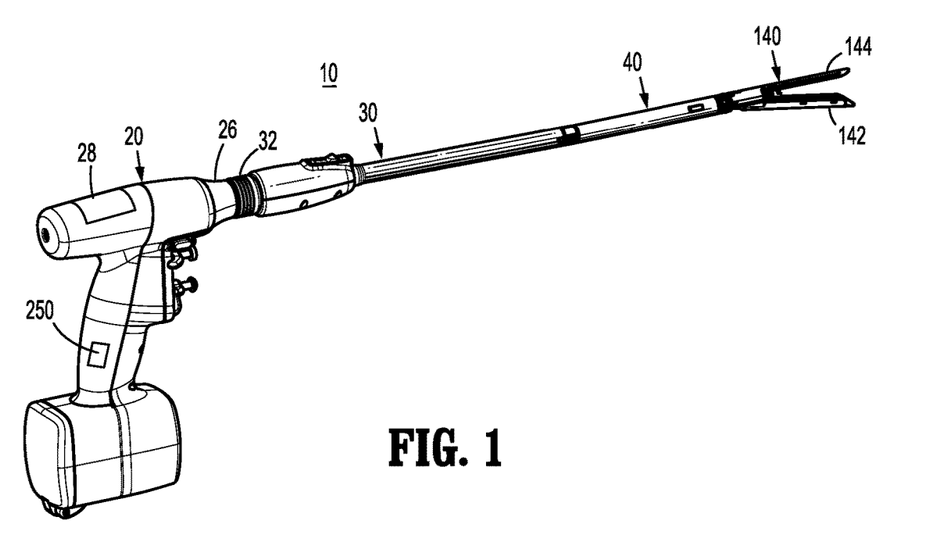
FIG. 1 is a perspective view of a surgical instrument provided in accordance with the present disclosure including a handle, an adapter coupled to the handle, and a loading unit coupled to the adapter.
Figure 2:
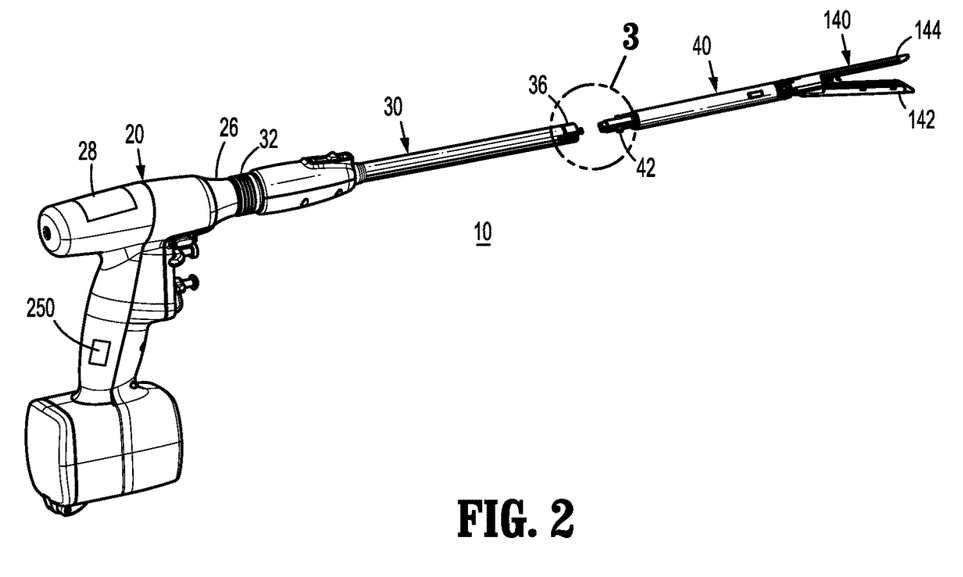
FIG. 2 is a perspective view of the surgical instrument of FIG. 1 with the loading unit separated from the adapter.
Figure 3:
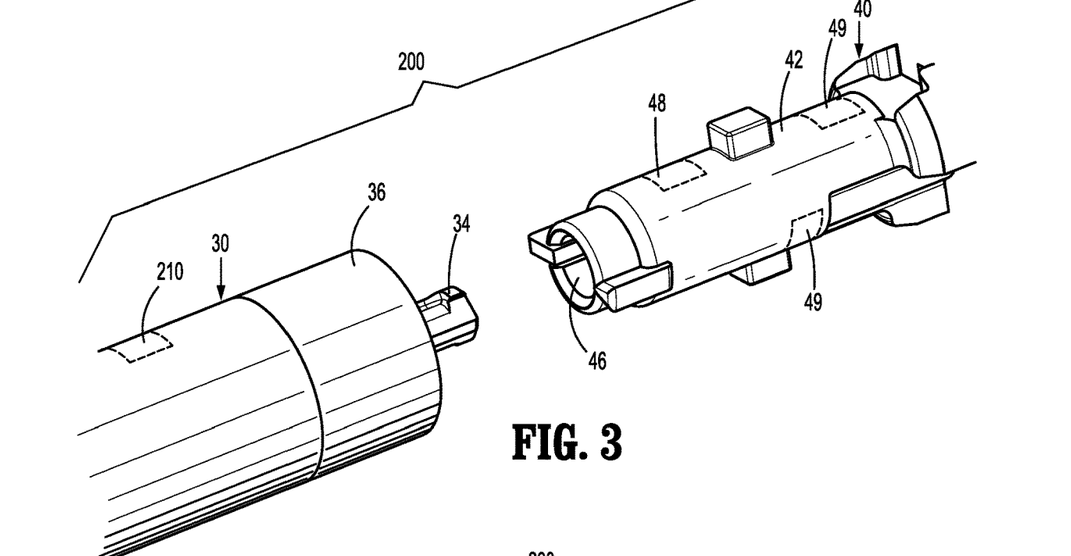
FIG. 3 is an enlarged view of the indicated area of detail of FIG. 2.

Referring now to FIGS. 1-3, a surgical instrument 10 is provided in accordance with the present disclosure including a handle 20, an adaptor 30, and a loading unit 40. The adaptor 30 includes a proximal portion having a handle connector 32. The handle 20 defines an adaptor receiver 26 for receiving the handle connector 32 to releasably couple the adaptor 30 to the handle 20. The loading unit 40 has a proximal portion includes a loading unit connector 42. The adaptor 30 has a distal portion that defines a loading unit receiver 36 that is positioned to releasably couple the disposable loading unit 40 to the adaptor 30. The loading unit 40 includes an end effector assembly 140 including first and second jaw members 142, 144 that are moveable relative to one another and are configured to act on tissue. It is contemplated that the adapter 30 may be fixed to the handle 20 such that the adapter 30 defines an elongate portion extending from the handle 20.

An exemplary embodiment of a surgical instrument is disclosed in commonly owned U.S. Pat. No. 9,055,943, the contents of which are hereby incorporated by reference in its entirety.

With particular reference to FIG. 3, the adapter 30 includes a translatable shaft 34 that extends distally through the loading unit receiver 36 and is configured to transfer mechanical energy from the adapter 30 to the loading unit 40 to actuate one or more functions of the end effector assembly 140 (FIG. 2), e.g., approximation and/or firing. The loading unit connector 42 of the loading unit 40 defines a shaft receiver 46 that receives the shaft 34 of the adapter 30. When the loading unit connector 42 is fully received within the loading unit receiver 36 the shaft 34 is coupled to the shaft receiver 46 such that translation of the shaft 34 actuates the end effector assembly 140.

Figure 4:
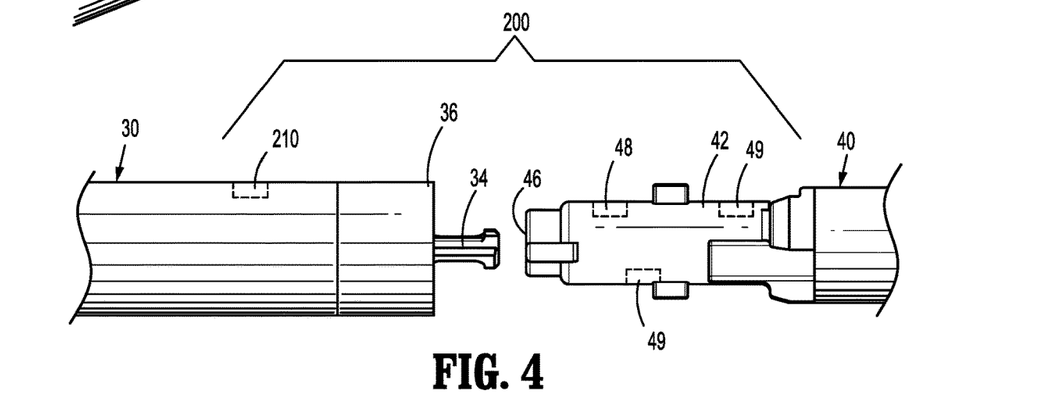
FIG. 4 is a side view of a distal portion of the adapter and a proximal portion of the loading unit of FIG. 3 with parts separated.
Figure 5:
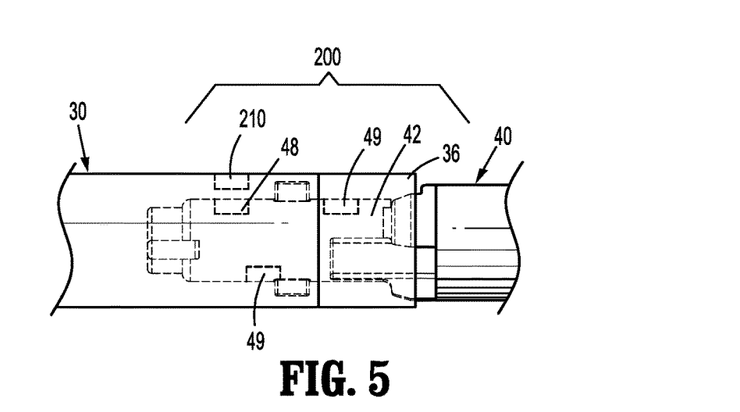
FIG. 5 is a side view of the distal portion of the adapter and the proximal portion of the loading unit of FIG. 3 with the loading unit coupled to the adapter.

With reference to FIGS. 3-5, the adapter 30 includes a contactless loading unit detection system 200 to determine the position of the loading unit connector 42 within the loading unit receiver 36. The loading unit detection system 200 includes a giant magneto-resistance integrated circuit (GMR IC) 210 embedded within a distal portion of the adapter 30 and the loading unit 40 includes a magnet 48 embedded within the loading unit connector 42. As detailed below, the GMR IC 210 is configured to output a differential voltage based upon the magnetic field induced in the GMR IC 210 by the magnet 48 of the loading unit 40. It will be appreciated that the differential voltage of the GMR IC 210 increases as a distance between the magnet 48 and the GMR IC 210 decreases.

In embodiments, the GMR IC 210 may be embedded within or adjacent the loading unit receiver 36 of the adapter 30 and/or the magnet 48 may be embedded within or adjacent the loading unit connector 42. By embedding both the GMR IC 210 and the magnet 48 within the loading unit receiver 36 and the loading unit connector 42, respectively, the loading unit detection system 200 does not include any exposed contacts. As such, fluid ingress into the loading unit detection system 200 is prevented. By preventing fluid ingress into the loading unit detection system 200, false indemnification of proper coupling of the loading unit 40 with the adapter 30 may be minimized.

The induced differential voltage of the GMR IC 210 is indicative of the position of the magnet 48 relative to the GMR IC 210 and thus, indicative of the position of the loading unit connector 42 of the loading unit 400 within the loading unit receiver 36 of the adapter 30. When the differential voltage of the GMR IC 210 reaches a predetermined threshold value, the loading unit connecter 42 is fully received within the loading unit receiver 36 (FIG. 5) such that the loading unit 40 is coupled to the adapter 30.

The GMR IC 210 may provide an analog or digital output indicative of the position of the loading unit connector 42 within the loading unit receiver 36. The handle 20 may include an indicator 28 configured to provide a visual indication of the position of the loading unit 40 within the adapter 30 and/or provide a visual indication when the loading unit 40 is coupled to the adapter 30.

In embodiments, the differential voltage of the GMR IC 210 may be used to identify the type of loading unit that is coupled to the adapter 30. For example, the loading unit 40 may include one or more additional magnets 49 that are/is configured to generate a unique magnetic field in the GMR IC 210 when the loading unit 40 is coupled to the adapter 30 such that the differential voltage of the GMR IC 210 is characteristic of the loading unit 40 that is coupled to the adapter 30. For example, in a linear stapling loading unit, the length of the staple line, staple size or sizes, characteristics such as whether the unit has a knife, dissection tip, buttress, etc., can be indicated. An indication that the unit has been used, is unused, or is within or beyond a certain prescribed number of uses, is contemplated.

The differential voltage of the GMR IC 210 is received within a GMR circuit, e.g., GMR circuit 220 (FIG. 6) or GMR circuit 320 (FIG. 7) detailed below, and outputted to a microprocessor 250 (FIG. 1) disposed within the handle 20 of the surgical instrument 10. The microprocessor 250 analyzes the output of the GMR circuit to detect and/or identify a loading unit 40 is properly coupled to the adapter 30.

Figure 6:
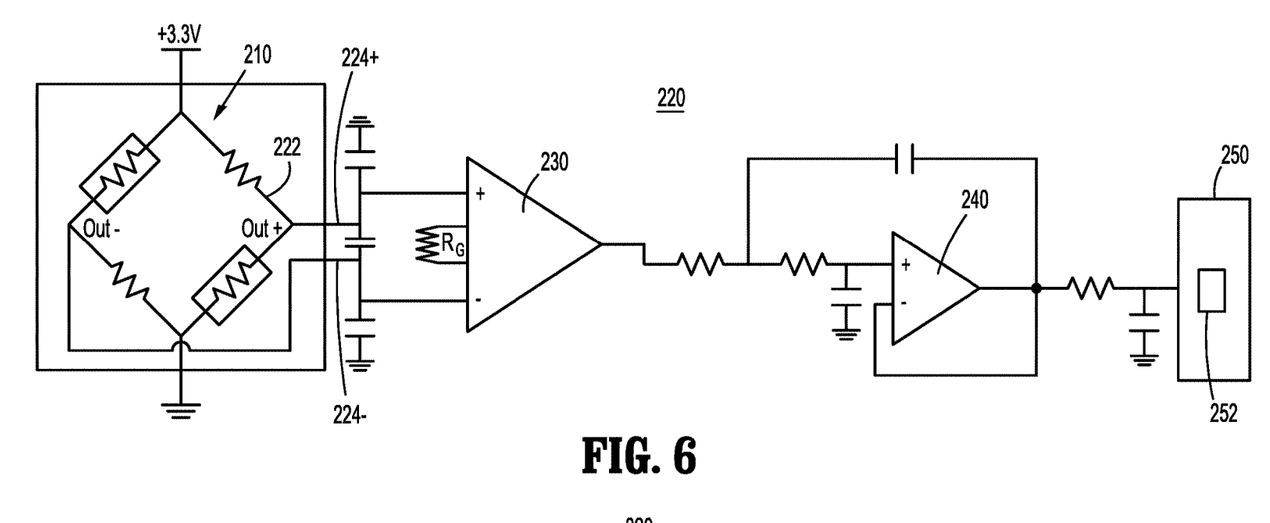
FIG. 6 is a schematic of a detection circuit provided in accordance with the present disclosure.

With reference to FIG. 6, a schematic of an illustrative GMR circuit 220 capable of detecting and identifying the presence and/or relative position of a loading unit, e.g., loading unit 40, is shown. The GMR circuit 220 includes the GMR IC 210 in the form of a partially shielded bridge 222 with positive and negative outputs 224+, 224−. The GMR IC 210 outputs a differential voltage signal based on a magnetic field induced in the GMR IC 210 by the magnets 48, 49 (FIG. 3). Specifically, as the magnetic field experienced by the GMR IC 210 varies, e.g., as the position of the magnets 48, 49 relative to the GMR IC 210 changes, the differential voltage of the output 224 varies. The outputs 224 of the GMR IC 210 are electrically coupled to an instrumentation amplifier 230 which outputs an amplified signal. The amplified signal may pass through a filter, e.g., low pass filter 240 before being transmitted to the microprocessor 250. The filtered signal of the low pass filter 240 may be transmitted to the analog to digital converter (ADC) 252 of the microprocessor 250 which analyzes the signal to identify the loading unit 40 based on a unique voltage signature and to determine when the loading unit 40 is coupled to the adapter 30. The microprocessor 250 may provide visual and/or audible indicia of the type of loading unit 40 and/or when the loading unit 40 is coupled to the adapter 30. The visual indicia may be provided on the display 28 (FIG. 1).

Figure 7:
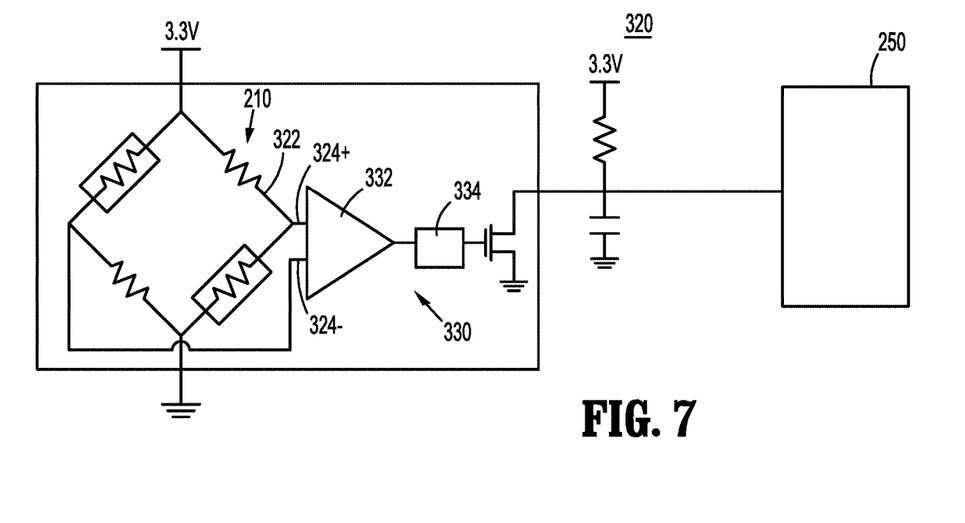
FIG. 7 is a schematic of another detection circuit provided in accordance with the present disclosure.

With reference to FIG. 7, a schematic of another illustrative GMR circuit 320 capable of detecting presence and/or relative position of a loading unit, e.g., loading unit 40, is shown. The GMR circuit 320 includes the GMR IC 210 in the form of a partially shielded bridge 322 with positive and negative outputs 324+, 324−. The GMR IC 210 outputs a differential voltage signal base on a magnetic field induced in the GMR IC 210 by the magnet 48. Specifically, as the magnetic field experienced by the GMR IC 210 varies, e.g., as the position of the magnet 48 relative to the GMR IC 210 changes, the differential voltage of the output 324 varies. The outputs 324 of the GMR IC 210 are electrically coupled to a comparator circuit 330 configured to detect when a signal from the GMR IC 210 exceeds a threshold value indicative of the position of the magnet 48 when the loading unit 40 is coupled to the adapter 30. The comparator circuit 330 may include an operational amplifier 332 and a latch 334 such that a connection signal is outputted from the latch 334 to the microprocessor 250 when the voltage of the GMR IC 210 is above the threshold value. It will be appreciated that no connection signal is outputted from the latch 334 when the voltage of the GMR IC 210 is below the threshold value. Alternatively, the latch 334 can be reversed such that the connection signal is outputted when the voltage of the GMR IC 210 is below the threshold value and is not outputted when the voltage of the GMR IC 210 is above the threshold value. The comparator circuit 330 may be integrated with the shielded bridge 322 to form an integrated GMR IC 210. The microprocessor may provide visual and/or audible indicia when the loading unit 40 is coupled to the adapter 30. The visual indicia may be provided on the display 28 (FIG. 1).

In some embodiments, the adapter 30 includes a translating element (not shown) which is translated proximally as the loading unit connector 42 is received within the loading unit receiver 36. In such embodiments, the magnet 48 and/or magnet 49 may be embedded within the translating element and the GMR IC 210 may be embedded within the adapter 30 at a position to determine the position of the magnet 48. In these embodiments, the entire detection system 200 may be disposed within the adapter 30 and/or the GMR IC 210 may be positioned in a central or proximal portion of the adapter 30 remote from the loading unit receiver 36. In some embodiments, the magnet 48 is embedded in the translating element and the magnets 49 are embedded within the loading unit connector 42 to induce a unique voltage in the GMR IC 210. For an exemplary translating element reference may be made to the detection link ring, the switch link ring, the switch link, the switch pin, or the switch button of the loading unit detection assembly of U.S. Patent Publication No. 2013/0324979, the entire contents of which are hereby incorporated by reference.

It will be appreciated that the handle 20 and the adapter 30 may also include a contactless detection system similar to the contactless detection system 200 detailed above to detect when and/or the type of adapter 30 coupled to the handle 20.

In any of the embodiments disclosed herein, the microprocessor 250 can be provided in a hand-held housing, a remote console, or some other device. The loading unit can be configured to be used in a robotic surgical system. Also, the contactless detection system can include technologies other than magnetic, such as induction.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. A loading unit detection system comprising:
   an elongate member defining a receiver;
   a loading unit including a connector configured to be received within the receiver to releasably couple the loading unit to the elongate member;
   a magnet supported on the connector, the magnet configured to translate relative to the elongate member as the connector is received within the receiver;
   a GMR IC embedded within the elongate member, the GMR IC configured to output a differential voltage in response to a magnetic field produced by the magnet of the loading unit, the differential voltage being indicative of a position of the loading unit within the receiver of the elongate member; and
   a secondary magnet embedded within the loading unit such that a differential voltage of the GMR IC induced by a combined magnetic field of the magnet and the secondary magnet is indicative of the position of the loading unit within the receiver of the elongate member and the type of the loading unit.

2. The system according to claim 1, wherein the magnet is embedded within the connector of the loading unit.

3. The system according to claim 1, further comprising an operational amplifier and a latch, the operational amplifier receiving the differential voltage from the GMR IC and transmitting amplified output to the latch, the latch having a first state when the amplified output is below a threshold and a second state when the amplified output is above the threshold.

4. The system according to claim 3, wherein the amplified output is below the threshold when the connector is in an uncoupled state with the receiver and above the threshold when the receiver is in the coupled state with the receiver.

5. The system according to claim 3, wherein the operation amplifier and latch are integrated with the GMR IC.

6. The system according to claim 1, further comprising an instrument amplifier and a filter, the instrument amplifier receiving the differential voltage from the GMR IC and outputting an amplified signal to the filter, the filter configured to output a filtered signal indicative of the position of the connector relative to the receiver and the type of the loading unit.

7. A surgical instrument comprising:
a handle;
an adapter releasably coupled to the handle;
a loading unit releasably coupled to the adapter; and
a loading unit detection system configured to detect coupling of the loading unit to the adapter, the loading unit detection system including:
a magnet supported on the loading unit, the magnet translating relative to the adapter as the loading unit is coupled to the adapter;
a GMR IC embedded within the adapter, the GMR IC configured to output a differential voltage in response to a magnetic field produced by the magnet of the loading unit, wherein the differential voltage produced by the GMR IC is indicative of a position of the loading unit within the adapter; and
an operational amplifier and a latch, the operational amplifier configured to receive the differential voltage from the GMR IC and transmit amplified output to the latch, the latch having a first state when the amplified output is below a threshold and a second state when the amplified output is above the threshold.

8. The surgical instrument according to claim 7, wherein the adapter defines a receiver and the loading includes a connector, the connector received within the receiver to releasably couple the loading unit to the adapter.

9. The surgical instrument according to claim 8, wherein the magnet is embedded within the connector of the loading unit.

10. The surgical instrument according to claim 9, wherein the GMR IC is embedded within the receiver of the adapter.

11. The system according to claim 8, wherein the amplified output is below the threshold when the connector is in an uncoupled state with the receiver and above the threshold when the receiver is in a coupled state with the receiver.

12. The surgical instrument according to claim 7, further comprising a microprocessor disposed within the handle, the microprocessor receiving a signal from the GMR IC indicative of the position of the loading unit relative to the adapter.

13. The surgical instrument according to claim 12, wherein the signal received by the microprocessor is indicative of the type of loading unit.

14. The system according to claim 7, wherein the operation amplifier and latch are integrated with the GMR IC.

15. A loading unit detection system comprising:
an elongate member defining a receiver;
a loading unit including a connector configured to be received within the receiver to releasably couple the loading unit to the elongate member;
a magnet supported on the connector, the magnet configured to translate relative to the elongate member as the connector is received within the receiver;
a GMR IC embedded within the elongate member, the GMR IC outputting a differential voltage in response to a magnetic field produced by the magnet; and
an instrument amplifier and a filter, the instrument amplifier receiving the differential voltage from the GMR IC and outputting an amplified signal to the filter, wherein the filter outputs a filtered signal indicative of a position of the connector relative to the receiver and a type of the loading unit.

16. The system according to claim 15, wherein the magnet is embedded within the connector of the loading unit.

* * * * *